United States Patent [19]

Banerjee

[11] Patent Number: 4,734,377

[45] Date of Patent: Mar. 29, 1988

[54] METHOD FOR INDIRECT DETECTION OF NONELECTROLYTES IN LIQUID CHROMATOGRAPHY

[76] Inventor: Sujit Banerjee, 3 Laurel Rd., RR #2, Rocky Point, Long Island, N.Y. 11778

[21] Appl. No.: 846,577

[22] Filed: Mar. 31, 1986

[51] Int. Cl.$^4$ ............................................. G01N 30/06
[52] U.S. Cl. ................................... 436/161; 73/61.1 C
[58] Field of Search ........................ 436/161; 210/656; 73/61.1 C

[56] References Cited

FOREIGN PATENT DOCUMENTS 1168705  6/1984  Canada ................................ 436/161

OTHER PUBLICATIONS

Sujit Banerjee et al., Indirect Detection of Non-Electrolytes in Liquid Chromatography with Additive Saturated Elements, Journal of Chromatography, 396 (1987) pp. 169–175.

Sujit Banerjee, General Indirect Detection of Nonelectrolytes in Liquid Chromatography by Solubility Enhancement, Analytical Chemistry, vol. 57, No. 13, Nov. 1985, pp. 2590–2592.

Sujit Banerjee, Solubility of Organic Mixtures in Water, Environmental Science & Technol, vol. 18, No. 8, Aug. 1984, pp. 581–591.

Banerjee et al., General Indirect Detection of Nonelectrolytes in Liquid Chromatography, Abstracts, Pittsburgh Conf. (1986), No. 376, p. 376.

Parkin, Journal of Chromatography, 287 (1984) 457–461.

Cortes et al., Journal of Chromatography, 295 (1984) 269–275.

Parkin et al., Journal of Chromatography, 314 (1984) 488–494.

Parkin, Journal of Chromatography, 303 (1984) 436–439.

Primary Examiner—David L. Lacey

[57] ABSTRACT

Method for indirect detection of transparent compounds in liquid chromatography through their interaction with a detectable additive present at saturation in the system. One embodiment of the invention includes a liquid chromatographic column, a detector and an eluent which contains an additive at saturation. The detector is tuned to a property of the additive. When an analyte that cannot be directly detected by the detector is injected, it interacts with the additive either by solubilizing it, or by displacing it from the stationary phase. When the analyte enters the detector it is indirectly detected by the induced change in concentration of the additive.

1 Claim, 3 Drawing Figures

METHOD FOR INDIRECT DETECTION OF NONELECTROLYTES IN LIQUID CHROMATOGRAPHY

BACKGROUND OF THE INVENTION

This invention relates generally to liquid chromatography and has particular reference to a novel method for indirect detection of nonelectrolytes.

The detection of nonelectrolytes is frequently limited by the insensitivity of the detector to the analyte. The problem is particularly acute for analytes which have no readily detectable spectroscopic, electrochemical or other property. The applicant is not aware of any prior art that has addressed itself to the problem of indirect detection of nonelectrolytes through the use of saturated additives in the eluent. The closest prior art known to the applicant is U.S. Pat. No. 3,929,410 issued to Schloss. This patent is directed to a method of indirect analysis where a saturated solution containing a known amount of radioactive standard is allowed to equilibrate with an unknown amount of the same compound in its unlabelled form, and quantitation of the unlabelled material is made on the basis of the amount of labelled material displaced. The present invention differs from that of the Schloss patent in that it does not require temperature changes to promote displacement of one material by another, is not restricted to radioactive materials, does not require the analyte and the standard to be of the same chemical structure, as will be described hereinafter.

The application of indirect detection to ion chromatography has been disclosed by Small and Miller in Canadian Pat. No. 1168705, and has been described by Cortes and Stevens (J. Chromatogr. 295(1984)269–275). In these references, a detectable ion is added to the eluent in a liquid chromatographic system, to serve as an indicator. When an analyte ion that is transparent to the detector is injected, it displaces an equivalent quantity of said indicator ion from the stationary phase. When the analyte enters the detector, the detector senses the decreased concentration of said indicator, and an indirect signal for the analyte ion is registered. This method is based on the principle of electroneutrality which requires the sum of the concentrations of analyte ion and indicator ion to be constant, since the concentration of the counterion, which is not retained by the stationary phase, is constant. The method applies only to ions, and cannot, therefore, be used for the detection of nonelectrolytes. As such, it differs from the present invention which is concerned only with the detection of nonelectrolytes.

The practice of indirect detection of nonelectrolytes has been described by Parkin (J. Chromatogr. 303(1984)436–439; J. Chromatogr. 287(1984)457–461), Parkin and Lau (J. Chromatogr. 314(1984)488–494), and Vigh and Leitold (J. Chromatogr. 312(1984)345–356). In these references, a detectable nonelectrolyte, hereinafter referred to as the additive, is added to the eluent to serve as an indicator. When a transparent analyte is injected, it disturbs the partitioning of the additive between the stationary phase and the eluent. When the analyte enters the detector, the detector senses the altered concentration of the additive in the eluent, and generates a signal. The sensitivity of the procedure is poor, as explicitly recognized by Parkin (J. Chromatogr. 303(1984)436–439). The present invention differs from this prior art method in the important regard that the additives used are present at saturation in the eluent. This novel feature leads to a very substantial improvement in the sensitivity of detection as will be described hereinafter.

Other prior art developed in the course of a preliminary search consists of U.S. Pat. Nos. 4,223,020; 3,222,525; 2,954,333 and 3,623,840.

SUMMARY OF THE INVENTION

The present invention has as its principal objective the provision of a method for indirectly detecting nonelectrolytes in liquid chromatography. Stated another way, the invention operates to induce a signal from an analyte which is not directly detectable, or is directly detectable with poor sensitivity in the system.

The signal is induced through the interaction between the analyte and an additive which is used as an indicator. The additive is present in the eluent at saturation, and is readily detectable by the detector. The apparatus of the invention in one embodiment thereof is essentially comprised of a chromatographic column, a detector, and an eluent which contains an additive at saturation, and a means for pumping the eluent through the column and into the detector. The apparatus also includes means for recording the output of the detector which is tuned to a suitable property of the additive. When a sample is injected at the head of the column, it interacts with the additive. As a result, the concentration of additive in the immediate vicinity of the analyte is altered. When the analyte emerges from the column and enters the detector, it can be indirectly detected by the induced change in concentration of the additive.

DESCRIPTION OF THE PREFERRED EMBODIMENTS

Figure 1:
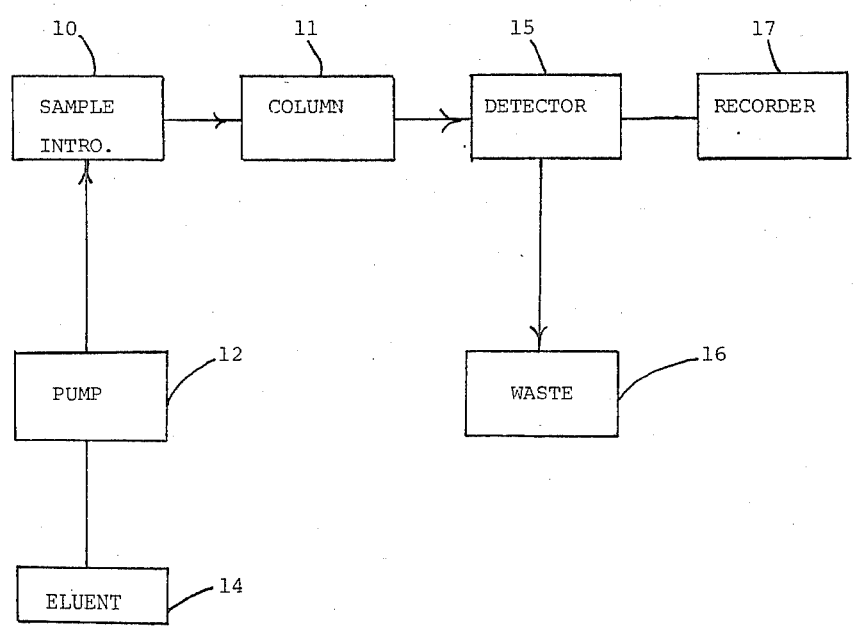
FIG. 1 is a diagrammatic illustration in the form of a flow chart of a prior art chromatographic apparatus.

Reference is now made to the drawings, and in particular to FIG. 1 illustrating prior art chromatographic apparatus. In FIG. 1, the sample which may contain a mixture of analytes is mixed with a suitable eluent as indicated at 10, and the resulting solution is introduced under pressure into a chromatographic column 11. The eluent is delivered to the column by a pump 12 which brings the eluent from a reservoir 14 or other source. The column 11 can be any one of a number of types whose constructions are well known in the art.

The outflow from the column passes through a known type of detector 15, as for example a photometric detector, and from thence to waste as indicated by 16. The output from the detector is recorded by a recording device 17 of a known type.

Eluents used for detection of nonelectrolytes in prior art chromatography consist of mixtures of one or more of solvents such as water, methanol, acetonitrile and hexane. The selection of solvents is made on the basis of their effect on the retention of analyte on the column.

In the method embodying the invention, an additive is added to the eluent at concentrations equal to or approaching saturation in the eluent. An essential property of the additive is that it must be detectable by the detector 15. The eluent is pumped through the column until equilibrium is reached. When an analyte is injected in 10 and enters the column 11, it interacts with the additive. The nature of the interaction depends on whether the analyte is strongly retained or weakly retained on the column with respect to the additive.

In a situation where an analyte is retained on the column to a lesser extent than the additive, its interaction with the stationary phase of the column is weaker than that between additive and said stationary phase. However, the analyte may be able to solubilize additive from the stationary phase into the eluent. In this event, the analyte carries the solubilized additive with it during its progress through the column. When the analyte leaves the column and enters the detector, a signal is induced since the detector is sensitive to the additive. By this means, analytes which are not directly detectable by the detector may be indirectly detected through the additive.

Figure 2:
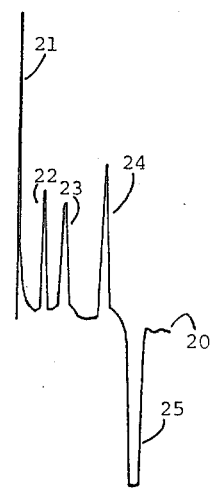
FIG. 2 is a chromatogram produced by the method of the invention where the analytes are retained on the column to a lesser degree than the additive.

The method of the invention has been employed using a Varian 5560 high performance liquid chromatograph, a Varian UV200 photometric detector set at 275 nm., a C-18 reversed phase column, an eluent of 70% methanol in water containing saturated p-terphenyl as the additive. Reference is now made to FIG. 2 where the baseline 20 represents a saturated solution of p-terphenyl. The mixture of analytes used contained pentane, hexane, and isooctane dissolved in methanol. The first signal 21, is of injected methanol which solubilizes p-terphenyl from the column. Signal 22 from pentane, 23 from hexane, and 24 from isooctane follow in sequence. The solubilized material creates a vacancy for p-terphenyl on the stationary phase. This vacancy elutes as a negative signal 25, at the retention volume of p-terphenyl.

Alkanes such as pentane, hexane and isooctane do not significantly absorb light at 275 nm., and their detection in the system is possible through the additive. It can therefore be seen that the additive provides an important means for chromatographic detection, and that the method can be used in any situation where additive and analyte interact, and where the detector responds to the additive.

In situations where the additive is present at a concentration lower than saturation, the interaction between analyte and additive is decreased, and the intensity of the signal induced by the analyte is also decreased.

If the analyte is retained to a greater extent on the column than the additive, then the interaction between analyte and the stationary phase of the column is stronger than the interaction between additive and said stationary phase. As a result, the analyte displaces additive from the stationary phase. A vacancy for the additive is thereby created on the stationary phase. The additive displaced is partially or completely dissolved in the solvent used to inject the analyte. When the analyte enters the detector, a negative signal is induced, since the detector senses the additive vacancy.

Figure 3:
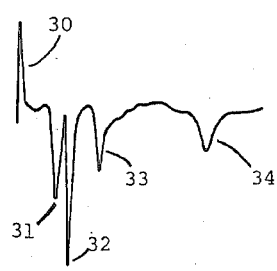
FIG. 3 is a chromatogram produced by the method of the invention where the analytes are retained on the column to a greater degree than the additive.

The method has been employed using the chromatograph, column, recorder and detector used in FIG. 1. The eluent was a 30% solution of methanol in water saturated with toluene. The mixture of analytes used contained chloroform, vinylidene chloride and 1,1,1-trichloroethane dissolved in a 50% solution of methanol. Reference is now made to FIG. 3. The first signal 30 is that of the injection solvent which solubilizes toluene from the column. Signal 31 is for the additive. This signal is negative since the amount of additive solubilized by the injection solvent is more than the amount of additive displaced by the analytes. Signal 32 is from chloroform, 33 is from vinylidene chloride, and 34 is from trichloroethane.

From the foregoing description, it will be apparent that the invention provides a novel and very advantageous method for the indirect detection of nonelectrolytic analytes, wherein the improvement lies in the use of eluents that are saturated with a detectable additive. It will be evident that if indirect detection of nonelectrolytes is practiced with the use of additives, then the particular use of saturated additives will be potentially the condition of greatest sensitivity. As will be understood by those familiar with the art, the invention may be embodied in other specific forms without departing from the spirit or essential characteristics thereof.

What is claimed is:

1. In a method for indirect detection of nonelectrolytic analytes in liquid chromatography wherein analytes are injected into a liquid chromatographic system comprising in combination an eluent containing an additive, a chromatographic column, and a detector tuned to said additive, and wherein said analytes are detected through concentration changes of the additive induced by said analytes, the improvement comprising the step of saturating the eluent with the additive to maximize the sensitivity of detection.

* * * * *